(12) United States Patent
Ahola et al.

(10) Patent No.: US 7,112,339 B1
(45) Date of Patent: Sep. 26, 2006

(54) COMPOSITIONS FOR CONTROLLED RELEASE OF A BIOLOGICALLY ACTIVE AGENT, AND THE PREPARATION THEREOF

(75) Inventors: Manja Ahola, Piikkiö (FI); Eija Säilynoja, Turku (FI); Jukka Salonen, Turku (FI); Risto Penttinen, Turku (FI); Antti Yli-Urpo, Littoinen (FI)

(73) Assignee: DelSiTech Oy, Turku (FI)

( * ) Notice: Subject to any disclaimer, the term of this patent is extended or adjusted under 35 U.S.C. 154(b) by 16 days.

(21) Appl. No.: 10/069,145

(22) PCT Filed: Aug. 22, 2000

(86) PCT No.: PCT/FI00/00710

§ 371 (c)(1),
(2), (4) Date: Feb. 22, 2002

(87) PCT Pub. No.: WO01/13924

PCT Pub. Date: Mar. 1, 2001

(30) Foreign Application Priority Data

Aug. 25, 1999 (FI) .................................. 19991806

(51) Int. Cl.
*A61K 9/14* (2006.01)

(52) U.S. Cl. .................. 424/484; 424/488
(58) Field of Classification Search ............. 424/484, 424/488, 422, 486, 400; 514/23, 54, 56, 514/772.1
See application file for complete search history.

(56) References Cited

U.S. PATENT DOCUMENTS 5,804,318 A * 9/1998 Pinchuk et al. ............. 428/421
5,858,280 A * 1/1999 Zhang et al. ............. 252/315.2

FOREIGN PATENT DOCUMENTS

| WO | WO 97/45367 | 12/1997 |
| WO | WO 00/50349 | 8/2000 |

OTHER PUBLICATIONS

Kuncova, G., Guglielmi, M., Dubina, P and Safar B. Lipase immobilized by sol-gel technique in layers. 1995. Collect. Czech. Chem. Commun. vol. 60, pp. 1573-1577.*

Chen, Hongmei et al.: "Preparation and Blood Compatibility of New Silica-chitosan Hybrid Biomaterials", *Art. Cells, Blood Subs. and Immob. Biotech.*, 26(4), 431-6 (1998).

Kim et al., "Heparin Immobilization onto Sol-gel Derived Organic-inorganic Hybrid Network", 127 *Chemical Abstracts* 14053 (1997).

Negent, et al., "Local Drug Delivery and Tissue Engineering Regulate Vascular Injury"; 128 *Chemical Abstracts* 145217 (1998).

* cited by examiner

Primary Examiner—Humera N. Sheikh
(74) Attorney, Agent, or Firm—James C. Lydon

(57) ABSTRACT

A composition for controlled release of a biologically active agent from a carrier. The biologically active agent is heparin or a related biologically active acidic polysaccharide and the carrier is a sol-gel derived silica xerogel. The xerogel is derived from a tetraalkoxysilane such as tetrethoxysilane (TEOS) and part of the tetraalkoxysilane is replaced by an organomodified alkoxysilane, preferably an akylsubstituted alkoxysilane. The invention also includes a method for the preparation of this composition.

7 Claims, 2 Drawing Sheets

COMPOSITIONS FOR CONTROLLED RELEASE OF A BIOLOGICALLY ACTIVE AGENT, AND THE PREPARATION THEREOF

This application is a U.S. national stage of International Application PCT/FI00/00710, filed Aug. 22, 2000 and published on Mar. 1, 2001 in the English language This application claims priority to foreign Finland Application No. 19991806 filed Aug. 25, 1999.

This invention concerns a composition for the controlled release of a biologically active agent from a carrier, and the preparation of said composition.

BACKGROUND OF THE INVENTION

The publications and other materials used herein to illuminate the background of the invention, and in particular, cases to provide additional details respecting the practice, are incorporated by reference.

By xerogel is meant a dried gel. Silica xerogels are partly hydrolyzed oxides of silicium. Hydrolyzed oxide gels can be produced by a sol-gel process, which has been used for producing ceramic and glass materials for several years.

The sol-gel process is based on hydrolyzation of a metal-alkoxide and subsequent polymerization of the metal hydroxides as follows:

$$Si(OR)_4 + H_2O \longrightarrow HO\text{—}Si(OR)_3 + ROH \quad\quad 1)$$

$$HO\text{—}Si(OR)_3 + 3\, H_2O + ROH \longrightarrow Si(OH)_4 + 4\, ROH \quad\quad 2)$$

$$Si(OH)_4 + Si(OH)_4 \longrightarrow (HO)_3Si\text{—}O\text{—}Si(OH)_3 + H_2O \quad\quad 3)$$

As the polymerization reaction progresses, additional chains, rings and three-dimensional networks are formed, and a gel, comprising water, the alcohol of the alkoxy group and the gel itself, is formed. The sol may also contain other additives, such as acids or bases, which are used as catalysts for the reaction. Further additives such as polyethylene glycol (PEG) can also be added to influence on the porosity of the gel. If alcohol and water are now extracted from the gel by washing and evaporation, a xerogel is obtained.

The polymerization of the remaining OH groups continues during the drying. The polymerization continues for a long time even after the gelation. This is called ageing. The further the polymerization proceeds, the more stable the gel or xerogel becomes. At room temperature, however, the polymerization will in fact stop after an ageing of a few weeks, and the xerogel will not become completely inert. If the temperature is raised, the polymerization reaction can be accelerated, the gel becomes more stable and shrinkage occurs, and internal stresses appear in the xerogel to an increasing degree.

The controlled release of therapeutic agents from biodegradable matrix has become increasingly important for implantable delivery systems, due to its advantages of safety, efficacy and patient convenience. The sol-gel technique offers new possibilities for incorporating biologically active agents within silica xerogels at room temperature process, and for controlling their release rates from silica xerogel matrix in time dependent manner (Nicoll et al. 1997; Ahola et al. 1998; Böttcher et al. 1998; Kortesuo et al., 1998; Sieminska et al., 1996). This sol-gel technology is cheap, versatile and simple, and silica xerogels produced by this technique are biocompatible and non-toxic materials (Kortesuo et al. 1998; Radin et al. 1998; Kortesuo et al. 1999). Earlier studies have shown that chemical and physical changes into the silica xerogel matrix have effect on the releasing behavior of biologically active agents because of the drug release from silica xerogel is the combined process of diffusion and matrix erosion.

A major concern with the use of artificial organs and biomedical devices is the untoward interactions of blood upon contacting a foreign surface. The most obvious complications are those related to the haemostatic mechanism, which can lead to thrombus formation and impaired function or occlusion of medical devices. Intravascular stenting is often used after angioplasty to prevent a reocclusion of the damaged vessel following dilation. One problem inherent to stent implantation is a possible restenosis. The process of restenosis is attributed to myointimal hyperplasia as well as to thrombus formation (Palmaz, 1993, Van Beusekom et al., 1993). The interaction of platelets with the stent surface may have significance not only due to their involvement in thrombus formation, but also by the release of platelet derived growth factor that may be included in the stimulation of smooth muscle cell growth (Palmaz, 1993, Ross, 1986). Heparin is routinely used for the prophylaxis of both surgical and medical thrombosis.

However, there is no disclosure or suggestion in prior art indicating that compositions for the controlled release of heparin could be achieved by incorporating heparin in a sol-gel derived silica xerogel, and that such a composition would be useful for treating and/or preventing thrombosis. Known heparin preparations are administered as injections. Thus, there is a great need for more convenient administration routes of heparin, especially for long acting, controlled release dosage forms of heparin.

OBJECTS AND SUMMARY OF THE INVENTION

The aim of this invention is to provide a composition for the controlled release of heparin or a related biologically active acidic polysaccharide, wherein said composition can be used for systemic or local prophylaxis and/or treatment of medical or surgical thrombosis.

Another object is to provide a method for the preparation of a composition for the controlled release of heparin or a related biologically active acidic polysaccharide. Thus, according to one aspect, this invention concerns a composition for controlled release of a biologically active agent from a carrier, wherein the biologically active agent is heparin or a related biologically active acidic polysaccharide and the carrier is a sol-gel derived silica xerogel. The xerogel is derived from a tetraalkoxysilane such as tetrethoxysilane (TEOS) and part of the tetraalkoxysilane is replaced by an organomodified alkoxysilane, preferably an alkylsubstituted alkoxysilane.

According to another aspect, this invention concerns a method for the preparation of a composition according to this invention. The method is characterized by the steps of a) hydrolyzing an alkoxysilane and an organomodified alkoxysilane in the presence of a catalyst, b) optionally adjusting the pH to a value suitable for the biologically active agent, c) adding the biologically active agent, d) allowing the hydroxysilane to polymerize, and optionally e) removing water and alcohol formed in the hydrolyzation from the mixture.

DETAILED DESCRIPTION OF THE INVENTION

Figure 1:
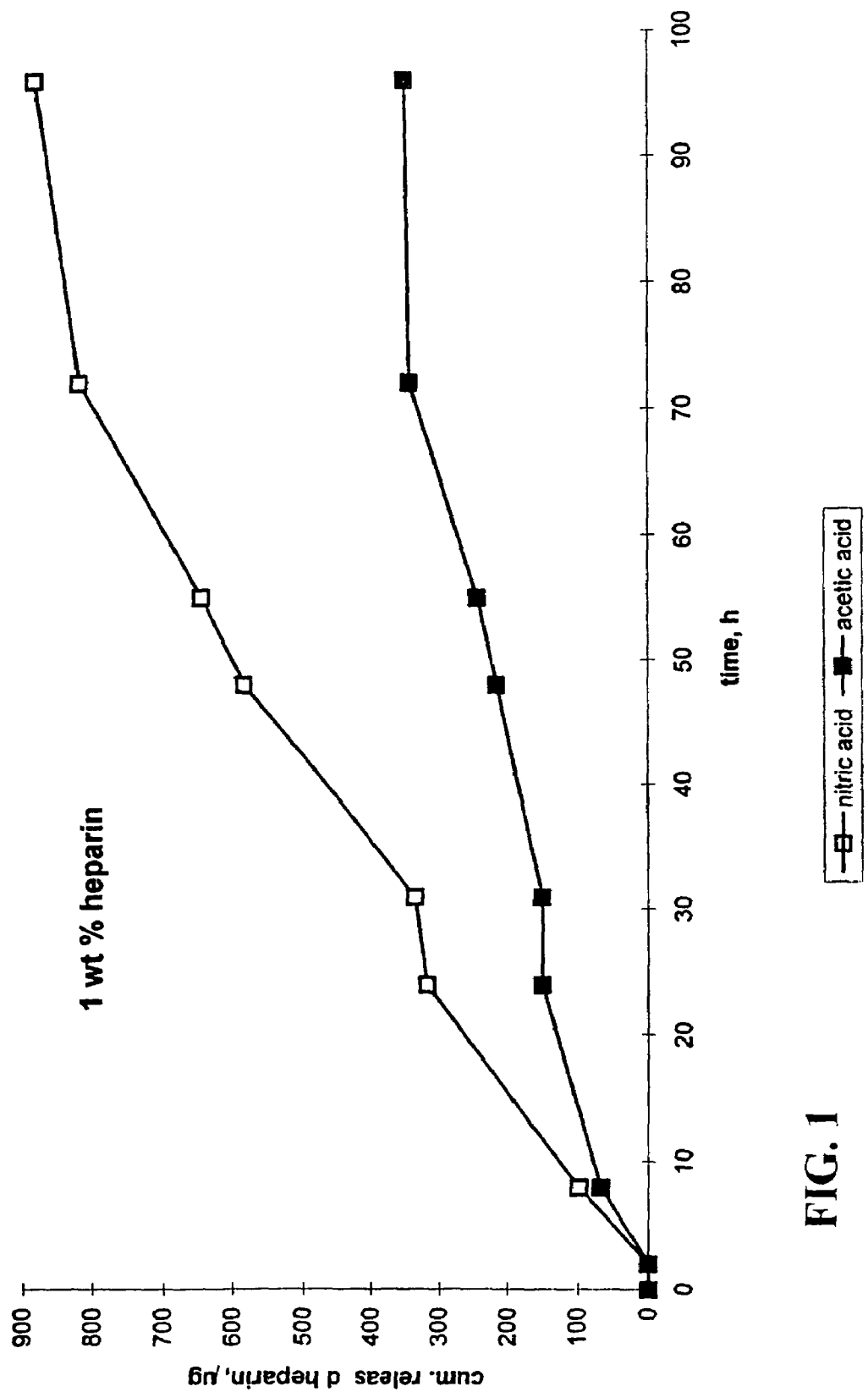
FIG. 1 shows the cumulative release of heparin versus time for formulations containing 1 weight-% of heparin, calculated on the sol, for xerogels made using nitric acid (open squares) or acetic acid (filled squares) as catalyst.

Heparin is a linear polysaccharide containing repeated units of six sugar residues, each consisting of an alternating sequence of sulfate derivatives on N-acetyl-D-glucosamine and D-iduronate (formula I). Heparin is a powerful anticoagulant and it is also a component of the extracellular matrix of blood vessels and promotes endothelial cell growth in vitro.

(ETES). In case about 25% of the amount of TEOS is replaced by one of the aforementioned organomodified alkoxysilanes, an increased release rate of the drug can be foreseen.

The amount of heparin is preferably about 5 to 15 weight-% calculated on the air dried xerogel.

Nitric acid or acetic acid is preferably used as catalyst.

The composition can be used for the treatment and/or prevention of surgical or medical thrombosis, for local or systemic use. Among the preferable administration routes can be mentioned subcutaneous or intramuscular dosage forms. Also long-acting injection forms could be prepared because the heparin loaded xerogel can be finished into small, injectable particles. According to a preferable embodiment, the formulation is an implantate to be placed in the close vicinity of the object undergone surgical operation. The formulation can also be used during the operation.

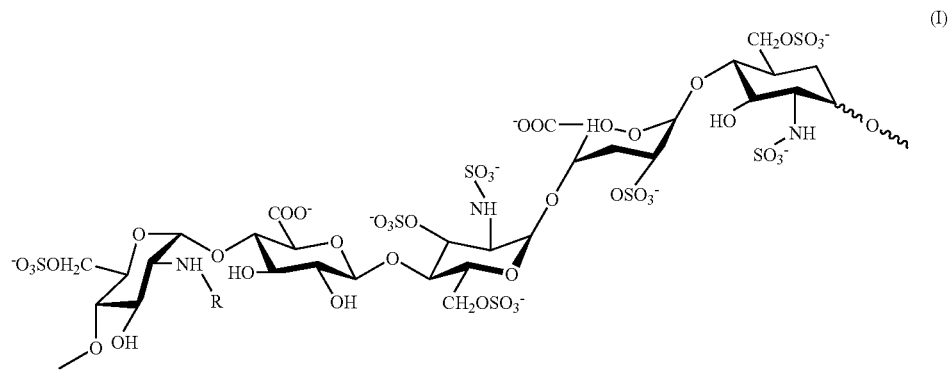

(I)

According to this invention, heparin can alternatively be replaced by a related biologically active acidic polysaccharide. As examples of such acidic polysaccharides having antithrombotic effects can be mentioned heparan sulfate proteoglycan, sulfonated hyaluronic acid and the like.

The heparin or the related biologically active acidic polysaccharide can either be of natural origin or biotechnically manufactured.

The purpose of the present study was to evaluate the suitability of sol-gel produced silica xerogel as the carrier matrix for controlled release of heparin or a related acidic polysaccharide. The influence of sol-gel parameters, such as catalysts or various alkoxysiloxanes, and the effect of heparin concentration were studied. Also the maintenance of biological activity of the drug after sol-gel process was tested. The release of heparin was linear according to zero order kinetics, and the release rates of different matrixes were found to be directly proportional to the drug load of the matrix. The release rate can be controlled by choosing the used catalyst in the sol-gel process. Other parameters affecting the structure and properties of the silica xerogels, such as the release rate of the drug, are the temperature, pH, drying and heating conditions of the silica sol. Also by chemical modification of silica xerogel network the release rate of heparin can be controlled.

The xerogel is derived from a tetraalkoxysilane such as tetraethoxysilane (TEOS). In case more brittle xerogels are desired, part of the tetraalkoxysilane (e.g. TEOS) is replaced by an organomodified alkoxysilane, preferably an alkylsubstituted alkoxysilane. As particularly preferred alkylsubstituted alkoxysilanes can be mentioned methyltriethoxysilane MeSi(OEt)$_3$(METES), dimethyldiethoxysilane Me$_2$Si(OEt)$_2$ (DMDES) or ethyltriethoxysilane EtSi(OEt)$_3$ The invention will be described more in detail in the Experimental section in the following non-limiting examples.

EXPERIMENTAL

Preparation of Silica Sol

The silica sol loaded with heparin was prepared by a two step sol-gel process using acid as a catalyst (Ellerby et al. 1992). The following reagents were used, tetraethoxysilane (TEOS) (Aldrich), deionized water, nitric acid (HNO$_3$) (Merck), acetic acid (CH$_3$COOH) (Merck), ammonium hydroxide (NH$_4$OH) (Merck)) and heparin sodium salt (Orion Corporation, Finland). The biological activity of the used heparin was 84 IU/mg measured by Factor Xa assay (HEPRN). The first step of the reaction series was a hydrolysis reaction between water and alkoxide. The mol ratio of the silica sol was TEOS:H$_2$O:HNO$_3$=1:15:0.0015 and TEOS:H$_2$O:CH$_3$COOH=1:15:0.026, respectively. Modification of the nitric acid catalyzed sol was carried out by co-hydrolysis of TEOS with the following organomodified (i.e. alkylsubstituted) alkoxysilanes: dimethyldiethoxysilane Me$_2$Si(OEt)$_2$ (DMDES) (Lancaster), methyltriethoxysilane MeSi(OEt)$_3$(METES) (Aldrich) or ethyltriethoxysilane EtSi(OEt)$_3$ (ETES) (Lancaster). For the partial substitution of TEOS, 10 or 25 mol-% organomodified alkoxysilane was used. After the first step, i.e. hydrolysis reaction, pH was raised to 4.5–4.8 with base (0.1 or 1 M NH$_4$OH) before heparin addition. The heparin sodium salt was first dissolved in the deionized water and then added to the hydrolysis solution. The concentration of heparin in silica sol ranged from 1 wt % to 4 wt % calculated on the sol, corresponding to 6.8–29.2 wt % in the air dried silica xerogel. The silica sol was cast into Blister plate wells, kept at 40° C. and 40% relative humidity for polycondensation and ageing. The aged silica gels were dried at 40° C. and 40% relative humidity to constant weight to obtain silica xerogels containing incorporated heparin. The formulations prepared are disclosed in Table 1.

TABLE 1

Formulation parameters used in the study.

| Formulation no. | Silane (mol - %) | | | | Catalyst | | Heparin conc. in the sol (wt %) |
|---|---|---|---|---|---|---|---|
| | TEOS | METES | ETES | DEDMS | acetic acid | nitric acid | |
| 1 | 100 | | | | x | | 1 |
| 2 | 100 | | | | x | | 1.5 |
| 3 | 100 | | | | x | | 2 |
| 4 | 100 | | | | x | | 3* |
| 5 | 100 | | | | x | | 4* |
| 6 | 100 | | | | | x | 1 |
| 7 | 90 | 10 | | | | x | 2 |
| 8 | 75 | 25 | | | | x | 2 |
| 9 | 90 | | 10 | | | x | 2 |
| 10 | 75 | | 25 | | | x | 2 |
| 11 | 90 | | | 10 | | x | 2 |
| 12 | 75 | | | 25 | | x | 2 |

*water/TEOS ratio = 24

In Vitro Release Experiments

Dissolution Test

The dissolution profiles of heparin and silica from the silica xerogel matrixes were studied in a shaking water bath at 37° C. Simulated body fluid (SBF) was used as a dissolution medium. SBF was prepared by dissolving reagent grade NaCl, $NaHCO_3$, KCl, $K_2HPO_4 \times 3H_2O$, $MgCl_2 \times 6H_2O$, $CaCl_2 \times 2H_2O$, $Na_2SO_4$ in deionized water (Table 2). The solution was buffered with tris(hydroxymethyl)aminomethane (TRIZMA) and hydrochloride acid (HCl) at physiological pH 7.40. The composition of inorganic ions emulated that of human blood plasma.

TABLE 2

| Reagent | concentration (mM) |
|---|---|
| NaCl | 136.8 |
| $NaHCO_3$ | 4.2 |
| KCl | 3.0 |
| $K_2HPO_4 \times 3H_2O$ | 1.0 |
| $MgCl_2 \times 6H_2O$ | 1.5 |
| $CaCl_2 \times 2H_2O$ | 2.5 |
| $Na_2SO_4$ | 0.5 |
| TRIZMA | 50 |

The silica xerogel sample was immersed in 50 ml SBF in a polyethylene bottle covered with a tight lid. Alternately, 5 ml sample or the whole medium was withdrawn from each flask and replaced immediately with fresh medium. Three parallel samples were used.

Toluidine Blue Test

The total amount of heparin dissolved was measured by a colorimetric toluidine blue method (Smith et al., 1980) modified to our purposes. 0.005% toluidine blue solution was prepared in 0.01 N HCl containing 0.2% NaCl. Standard heparin solution was prepared by 20 mg heparin, diluted to 100 ml with SBF solution. The standard dilutions were between 5 and 40 µg of heparin in the sample. One and one quarter (1.25) ml of toluidine blue solution (0.005%), and 1.25 ml of in SBF solution were pipetted into test tubes. All the tubes were mixed vigorously by Vortex for 30 s. Next, 2.5 ml of hexane was added to the tubes and they were shaken for another 30 s to separate the heparin-dye complex formed. The aqueous layers of the tubes were sampled and if necessary diluted with SBF. The absorbance at 631 nm was measured within 30 min with Shimadzu UV-Vis-1601 Spectrophotometer.

Silica Determination

Degradation of the silica xerogel matrix was determined by measuring dissolved $Si(OH)_4$ as a molybdenum blue complex by UV-spectrophotometer at 820 nm (Koch and Koch-Dedic, 1974).

Thrombin Assay

The biological activity of heparin against thrombin formation was evaluated by the chromogenic method (Hall et al., 1984, Han et al., 1989). Heparin forms heparin-antithrombin III (ATIII)-thrombin (T) complex with ATIII in plasma. As illustrated in Scheme 1, the biological activity of heparin can be directly measured if excess amount of thrombin is used to make heparin-ATIII complexes and the amount of used thrombin is determined with Chromozym TH. Thrombin acts as a catalyst in the splitting of paranitroaniline (pNA) from Chromozym TH. The pNA release rate was determined by measuring the absorbance at 405 nm. The experiments were performed according the route illustrated in Scheme 1 comprising the steps:

1. Heparin+ATIII→heparin/ATIII complex
2. Heparin/ATIII+thrombin (excess)→heparin/ATIII/thrombin+residual thrombin
3. Chromozym TH→peptide+pNA (measured at 405 nm)

Platelet poor plasma (57 µl) was diluted with Tris buffer solution (245 µl, pH 8.3) and 150 µl sample solution in a 5 ml test tube. The test tubes were stirred and incubated at 37° C. for 3 min. 150 µl of thrombin solution (8 IU/ml, Sigma T-7009, St. Louis, Mo., USA) was added, mixed and incubated for additional 60 s at 37° C. Then 150 µl Ghromozym TH solution (1.13 mM, previously heated to 37° C., Tos-Gly-Pro-Arg-pNA, Boehringer Mannheim, Mannheim, Germany) was added, mixed and incubated for 310 s at 37° C. The reaction was stopped by adding 450 µl of 50% acetic acid. The samples were analyzed spectrophotometrically at 405 nm using a Shimadzu UV-1601 spectrophotometer. Heparin standards between 0.2 and 1.0 IU/ml were done as samples. The relative biological activity was calculated by comparing the thrombin neutralization of immobilized heparin with that of free heparin. The rate of increase in absorbance at 405 nm due to the appearance of the chromophore, p-nitroaniline, is linearly and inversely related to the effective activity by means of standard curve.

Scheme 1

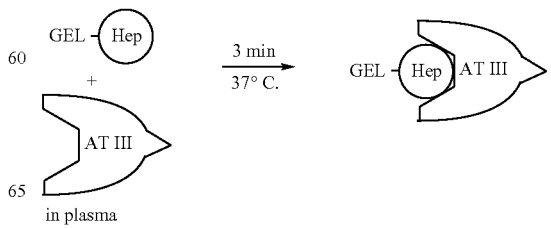

Stage I

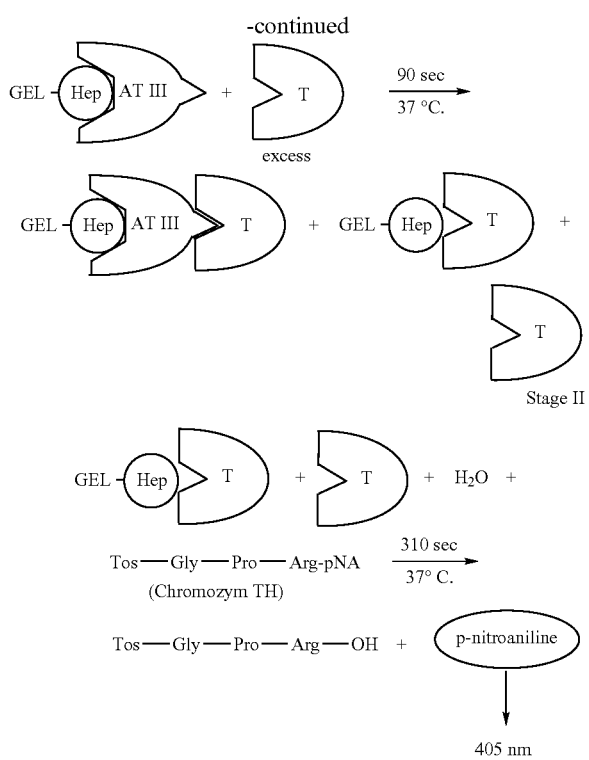

RESULTS

The test results of certain formulations prepared are shown in Table 3.

Heparin release from the different formulations examined occurred during the dissolution of the matrix. At the end of dissolution period (96 h), 10% of the matrix in the tested formulations was dissolved, measured by silica content, and the same amount of heparin was released, suggesting that the heparin release is controlled by matrix erosion. Heparin release from a formulation containing 1 wt-% of heparin in the sol was identical to the rate of the matrix dissolution. Heparin release from the matrix was measured with toluidine blue method and according to silica xerogel matrix erosion studies. This implies that drug release may be described as a process that is controlled mainly by erosion of the matrix. In addition, the porosity of the matrix have an noticeable effect on the dissolution process. Especially in the case of small molecules, drug release is combined process of diffusion and matrix erosion.

Effect of Catalyst

A model formulation containing 1 wt % heparin in the sol in order to investigate the influence of the used catalyst in the hydrolysis process on the dissolution rate of heparin. Silica xerogel monoliths were prepared using either acetic acid or nitric acid catalyst. At the pH 2.5 the hydrolysis step was faster while nitric acid was used, 45–60 min, than the one carried out by using acetic acid, 5 hours. According to the literature (Brinker & Scherer), the rate and extent of the hydrolysis reaction is most influenced by the strength and concentration of the acid catalyst. All strong acid behaved similarly, whereas weaker acid required longer reaction times to achieve the same extent of the reaction. The reaction rate with weaker acid can be accelerated by increasing the used reaction temperature.

In the present case, the pH of the sol was raised to 4.5–4.8 with $NH_4OH$ after hydrolysis step to avoid the precipitation of heparin. The rate of gel formation, ie. the rate of the condensation reactions, is influenced by pH and has a considerable influence on the three dimensional structure of silica network (Brinker & Scherer). The gel time is longest near the isoelectric point (IEP) of silica, pH 2, and decreases with increasing pH of the sol (Iler, 1979). Near the IEP there is no electrostatic particle repulsion. Slower kinetics produce linear silica aggregates and more condensed structure but when the pH is raised, gel formation rate increases resulting in more porous structure.

FIG. 1 shows the cumulative release of heparin versus time for formulations containing 1 weight-% of heparin, calculated on the sol, for xerogels made using nitric acid or acetic acid catalyst. When fitted to zero order model the heparin release was linear with both catalysts. The dissolution rate was 60% slower from acetic acid catalyzed gels compared to gels catalyzed with nitric acid. This may be due to the higher density of the xerogel prepared by acetic acid catalyst (formulation No. 1, Table 3) compared to that prepared by nitric acid catalyst (formulation No. 6, Table 3).

Effect of Heparin Concentration

Figure 2:
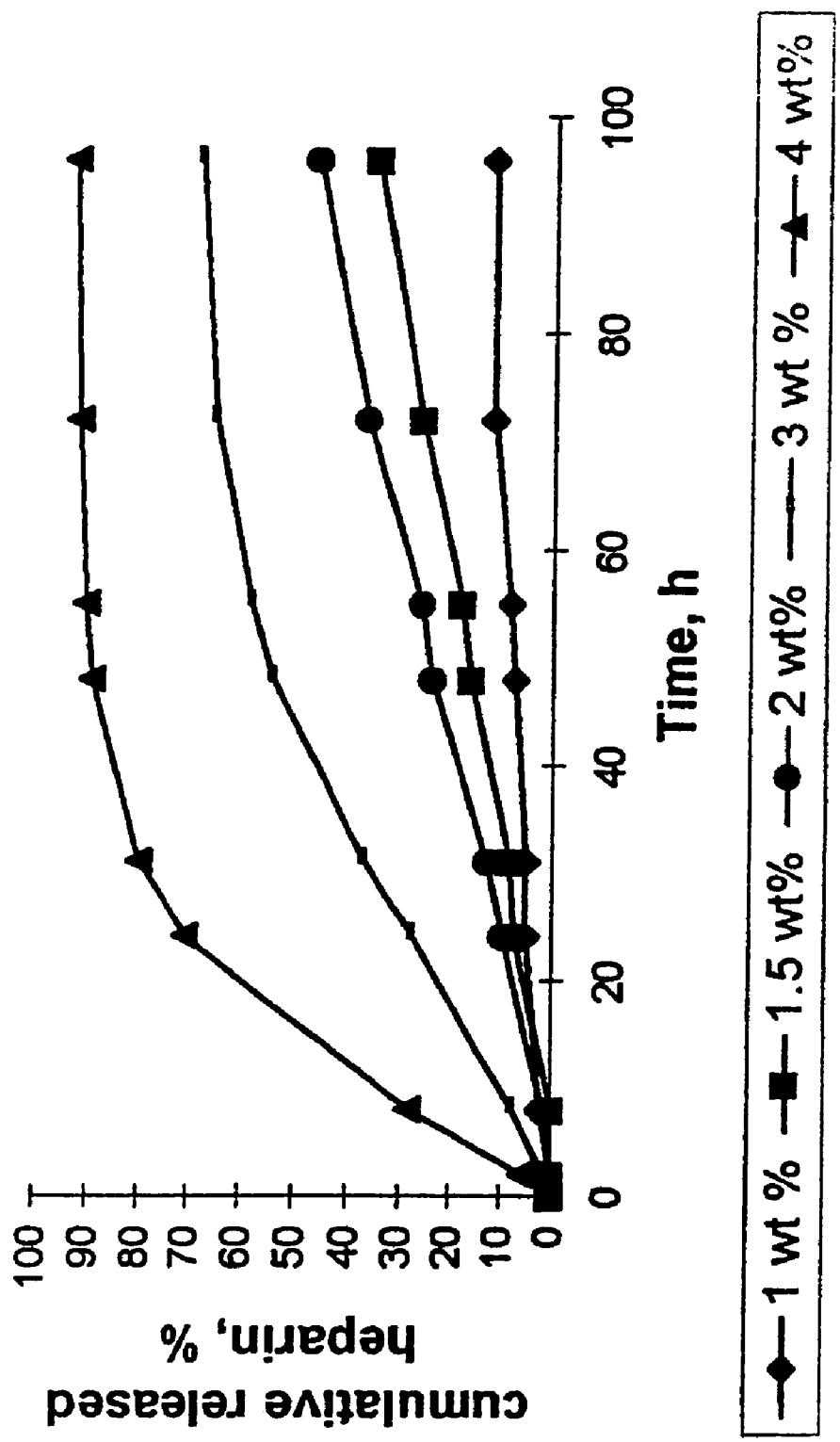
FIG. 2 shows the cumulative release of heparin in percent versus time for formulations containing 1, 1.5, 2, 3 and 4 weight-% of heparin, calculated on the sol, for xerogels made using acetic acid as catalyst.

The effect of heparin concentration was studied by using both nitric and acetic acids as the catalyst. The release of heparin from silica xerogel matrix prepared at pH 4.8 (acetic acid catalysed) with the different loads of heparin sodium salt in the silica sol (1, 1.5 and 2 wt %, calculated on the sol) was linear according to zero order kinetics (FIG. 2). The release rates of these different matrixes were found to be directly proportional to the drug load of the matrix. Similar releasing profiles, zero order, were observed while nitric acid was used. Correlation between the release rate and the drug load can be used to predict the release rate of heparin from the silica xerogel matrix with the same surface area. The matrix erosion was also linear and the heparin concentration did not have an influence on the degradation rate of the matrix. These findings are in accordance with our previous paper (Ahola et al., 1999).

Effect of Organomodified Alkoxysilanes

The release rate of biologically active molecules can be influenced by chemical modification of the silica xerogel matrix (Böttcher et al., 1998). Incorporation of organomodified alkoxysilanes into hydrolysis step with TEOS results increasing hydrophobicity of the matrix and changes in porosity. In this study, modification of nitric acid catalyzed sol with co-hydrolysis of TEOS with METES, ETES or DMDES, was carried out. Partial substitution of TEOS with 10 or 25 mol-% of organomodified alkoxysilanes were used. This partial substitution results in more brittle materials. All monoliths were broken during dissolution period which of course have an effect on the release rate. The addition of 10 mol-% organomodified alkoxysilane into the sol did not have any significant effect on the release rate of heparin. The release of heparin was linear according to zero order kinetics from all formulations containing 10 mol-% of organomodified alkoxysilane. When the amount was increased to 25 mol-%, the release behaviour of heparin was better fitted to first order kinetics indicating diffusion controlled process. The release rate of the drug was increased 20 to 40% when 25 mol-% ETES and DMDES were used. Another reason for the faster releasing rate, besides the brittle structure, can be decreasing possibility to form hydrogen bonds between silica network and heparin.

TABLE 3

| Formulation no. | Dissolution of heparin b = slope (%/h) | Degradation of the matrix | Density (g/cm$^3$) (SD) |
|---|---|---|---|
| 1 | r = 0.9772 b = 0.133 | r = 0.9964 b = 0.101 | 1.670 (0.012) |

TABLE 3-continued

| Formulation no. | Dissolution of heparin b = slope (%/h) | Degradation of the matrix | Density (g/cm$^3$) (SD) |
|---|---|---|---|
| 2 | r = 0.9975<br>b = 0.382 | r = 0.9995<br>b = 0.074 | 1.675 (0.017) |
| 3 | r = 0.9980<br>b = 0.512 | r = 0.9992<br>b = 0.071 | 1.736 (0.020) |
| 4 | r = 0.9986 (2–48 h)<br>b = 1.166 | r = 0.9971<br>b = 0.089 | 1.824 (0.032) |
| 5 | r = 0.9466 (2–48 h)<br>b = 1.853 | r = 0.9919<br>b = 0.099 | 1.889 (0.007) |
| 6 | r = 0.9822<br>b = 0.341 | r = 0.9997<br>b = 0.085 | 1.635 (0.009) |

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Ahola, M., P. Kortesuo, et al. (1998). Effect of processing parameters on the structure of silica xerogel matrix and on the release rate of toremifene citrate and silica. 24th Annual Meeting of the Society for Biomaterials, San Diego, USA, pp. 343.

Ahola, M., Kortesuo, P. Kangasniemi, I., Kiesvaara, J. and Yli-Urpo, A. Silica xerogel carrier system for controlled release of toremifene citrate. Submitted to International Journal of Pharmaceutics, 1999.

C. J. Brinker and G. W. Scherer, Sol-Gel Science; The Physics and Chemistry of Sol-Gel Processing, Academic Press, Inc., San Diego, USA, 1990.

Böttcher, H., P. Slowik, et al. (1998). Sol-gel carrier systems for controlled drug delivery. J. Sol-Gel Sci. Tech., 13, 277–281.

Cihlar, J., Colloids Surface A; Physicochem. Eng. Aspects, 70 (1993) 239–251.

Ellerby, L. M., Nishida, C. R., Nishida, F., Yamanaka, S. A., Dunn, B., Selverstone Valentine, J., and Zink, J. I., Science, 28 (1992) 1113–1115.

Hall, R. and Malia, R. G. (eds.), Medical Laboratory Haemotology, 1$^{st}$ edn. Butterworths, London, 1984, pp. 629–632.

Han, D. K., Jeong, S. Y. and Kim, Y. H., Evaluation of blood compatibility of PEO grafted and heparin immobilized polyurethanes. J. Biomed. Mater. Res.: Appl. Biomater., 1989, 23, 211–228.

HEPRN, Test methodology for the aca® discrete clinical analyzer, Du Pont Company, Wilmington, Del. 19898, USA.

Iler, R. K., 1979. The chemistry of silica. John Wiley, New York.

Kortesuo, P., Ahola, M. et al. (1998). The evaluation of biocompatibility and degradation of non-sintered silica xerogel carrier materials in vivo. Biomaterials., accepted.

Kortesuo, P., Ahola, M. et al. (1999). Sol-gel processed sintered silica xerogel as a carrier in controlled drug delivery. J. Biomed. Mater. Res., 44(2), 162–167.

Nicoll, S. B., S. Radin, et al. (1997). In vitro release kinetics of biologically active transforming growth factor-β1 from a novel porous glass carrier. Biomaterials., vol. 18, 853–859.

Palmaz, J. C., (1993) AJR, 160, 613.

Radin, S., G. El-Bassyouni, et al. (1998). Tissue reactions to controlled release silica xerogel carriers. In Bioceramics 11, World Scientific, New York,. Pp. 529–532.

Ross, R. (1986), N. Engl. J. Med. 314, 488-

Sieminska, L, Ferguson, M., Zerda, T. W. and Couch, E., 1996. Diffusion of steroids in porous sol-gel glass: Application in slow drug dliery. J. Sol-Gel. Sci., 8, 1105–1109.

P. K. Smith, S. Mallia, and G. T. Hermanson, Analytical Biochemistry, 109 (1980) 466.

Van Beusekom, H. M. M., Van der Giessen, W. J., Van Suylen, R. J., Bos, E., Bosman, F. T. and Serruys, P. W. (1993), JAAC 21, 45-.

The invention claimed is:

1. A composition for controlled release of a biologically active agent from a carrier, said composition consisting essentially of a biologically active agent which is heparin or a related biologically active acidic polysaccharide, and a carrier which is a sol-gel derived silica xerogel, wherein the xerogel is derived from tetraethoxysilane and part of the tetraethoxysilane is replaced by an alkylsubstituted alkoxysilane, and wherein said composition is biodegradable.

2. The composition of claim 1, wherein said alkylsubstituted alkoxysilane is a member selected from the group consisting of methyltriethoxysilane (METES), dimethyldiethoxysilane (DMDES) and ethyltriethoxysilane (ETES).

3. The composition of claim 1, wherein said biologically active agent is heparin and which is present in an amount of 5 to 30 weight percent, calculated on the air dried xerogel.

4. The composition of claim 1, wherein said alkylsubstituted alkoxysilane is present in said xerogel in an amount effective to increase a release rate of said biologically active agent from said xerogel in comparison to a xerogel prepared from tetraethoxysilane only.

5. A method for the preparation of a composition for controlled release of a biologically active agent from a carrier, said method consisting essentially of
   a) hydrolysing an alkoxysilane and an alkyl substituted alkoxysilane in the presence of a catalyst,
   b) optionally adjusting the pH to a value suitable for the biologically active agent,
   c) adding the biologically active agent,
   d) allowing the hydroxysilane to polymerize, and optionally
   e) removing water and alcohol formed in the hydrolyzation from the mixture, wherein said composition consists essentially of a biologically active agent which is heparin or a related biologically active acidic polysaccharide, and a carrier which is a sol-gel derived silica xerogel, wherein the xerogel is derived from tetraethoxysilane and part of the tetraethoxysilane is replaced by an alkylsubstituted alkoxysilane, and wherein said composition is biodegradable.

6. The method of claim 5, wherein said alkylsubstituted alkoxysilane is at least one member of the group consisting of methyltriethoxysilane (METES), dimethyldiethoxysilane (DMDES) and ethyltriethoxysilane (ETES).

7. The method of claim 5, wherein nitric acid or acetic acid is used as a catalyst.

* * * * *

UNITED STATES PATENT AND TRADEMARK OFFICE
CERTIFICATE OF CORRECTION

| | | |
|---|---|---|
| PATENT NO. | : 7,112,339 B1 | Page 1 of 1 |
| APPLICATION NO. | : 10/069145 | |
| DATED | : September 26, 2006 | |
| INVENTOR(S) | : Ahola et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 16 days Delete the phrase "by 16 days" and insert -- by 124 days--

Signed and Sealed this

Twenty-sixth Day of June, 2007

JON W. DUDAS
*Director of the United States Patent and Trademark Office*